United States Patent
Akgün et al.

(10) Patent No.: US 10,766,853 B2
(45) Date of Patent: Sep. 8, 2020

(54) CATALYTIC PROCESS FOR PREPARING N,N-DIMETHYLGLUCAMINE FROM N METHYLGLUCAMINE

(71) Applicant: Clariant International Ltd., Muttenz (CH)

(72) Inventors: Ertan Akgün, Ingolstadt (DE); Martin Link, Mühldorf (DE); Sarah Werner, Mühldorf (DE); Klaus Raab, Burgkirchen (DE); Peter Klug, Grossostheim (DE); Karl Scheitzeneder, Engelsberg (DE); Stefan Kreuzpointner, Töging (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

(21) Appl. No.: 16/495,370

(22) PCT Filed: Feb. 28, 2018

(86) PCT No.: PCT/EP2018/054856
§ 371 (c)(1),
(2) Date: Sep. 18, 2019

(87) PCT Pub. No.: WO2018/172025
PCT Pub. Date: Sep. 27, 2018

(65) Prior Publication Data
US 2020/0017435 A1 Jan. 16, 2020

(30) Foreign Application Priority Data
Mar. 20, 2017 (EP) .................................... 17161763

(51) Int. Cl.
*C07C 213/08* (2006.01)

(52) U.S. Cl.
CPC .................................. *C07C 213/08* (2013.01)

(58) Field of Classification Search
None
See application file for complete search history.

(56) References Cited

U.S. PATENT DOCUMENTS

| | | | |
|---|---|---|---|
| 4,190,601 A | | 2/1980 | Decker |
| 5,194,639 A | | 3/1993 | Connor |

FOREIGN PATENT DOCUMENTS

| | | | |
|---|---|---|---|
| CA | 2117007 | * | 9/1994 |
| DE | 2118283 | | 11/1972 |
| EP | 0142868 | | 5/1985 |
| EP | 0614881 | | 9/1994 |
| EP | 0663389 | | 7/1995 |
| GB | 908203 | | 10/1962 |
| WO | 9206073 | | 4/1992 |

OTHER PUBLICATIONS

International Search Report for PCT/EP2018/054856, dated May 2, 2018. 2 pages.

* cited by examiner

*Primary Examiner* — Sudhakar Katakam
*Assistant Examiner* — Jennifer C Sawyer
(74) *Attorney, Agent, or Firm* — Tod A. Waldrop

(57) ABSTRACT

The invention relates to a method for preparing aqueous solutions of N,N-dimethylglucamine, characterized by first preparing an adduct of N-methylglucamine and formaldehyde in water at temperatures of between 15° C. and 40° C., and subsequently reacting said adduct to N,N-dimethylglucamine in the presence of a metal catalyst under hydrogen pressure at 20-68° C., followed by secondary hydrogenation at 70-120 bar and 70-110° C. once hydrogen absorption at 20-68° C. is completed.

15 Claims, No Drawings

CATALYTIC PROCESS FOR PREPARING N,N-DIMETHYLGLUCAMINE FROM N METHYLGLUCAMINE

The N,N-dimethylglucamine (D-glucitol, 1-deoxy-1-(dimethylamino)-) described here is a valuable compound which is suitable for a host of commercial applications. These include, for example, its use as an additive in wetting agents, cleaning products, plasticizers, glidants and lubricants, and the like. There are also more recent fields of application in the manufacture of paints and inks, in crop protection, in medicine, and in cosmetics. The product, which is based on renewable raw materials, can also be used as a mild neutralizing agent or, in protonated form, as a hydrophilic cation. For this broad spectrum of applications, there are numerous quality requirements to be observed, which are not described in known processes for preparing N,N-dimethylglucamine.

The process described here allows the direct preparation of minimally colored N,N-dimethylglucamine solutions from readily commercially available N-methyl-glucamine under particularly mild conditions with the aid of an improved, two-stage process without costly and inconvenient purification.

Regarding the preparation of N,N-dimethylglucamine, the literature describes a number of processes, which, however, give rise to one or more disadvantages.

EP-0614881 describes the reaction of N-monoalkylpolyhydroxy compound with aldehydes in a ratio of 1:0.9-1.5 or 1:1.1-1.03 with subsequent hydrogenation over a metallic hydrogenation catalyst, e.g., Raney-Ni, to give the tertiary dialkylpolyhydroxyamine. This reaction requires a hydrogen pressure of 10 to 150 bar and temperatures of 70 to 150° C. More particularly the reaction is carried out in two reaction steps, in which a) first a secondary N-monoalkylpolyhydroxyamine (e.g., N-methylglucamine) is reacted with an aldehyde (e.g., formaldehyde) in a molar ratio of 1:0.90-1.5, preferably 1:1.03-1.1, in water as solvent at a temperature of 15 to 60° C., preferably of 20 to 40° C., under atmospheric pressure to give the N-monoalkylpolyhydroxyamine/aldehyde adduct, and b) the reaction product present in step a) (and consisting substantially of water and the adduct formed) is hydrogenated in the presence of a metallic hydrogenation catalyst with hydrogen at a pressure of 10 to 150 bar, preferably 30 to 100 bar, and at a temperature of 70 to 150° C., preferably 80 to 130° C., to give the tertiary dialkylpolyhydroxyamine (e.g., N,N-dimethylglucamine).

EP-0614881 describes the possibility of achieving high yields with this process; however, no further details are described regarding the workup of the crude reaction solution. The patent specification describes the implementation of the reaction in aqueous solution, but other than the melting point there is no information on quality parameters of the dimethylglucamine. This means that there must have been a crystallization from the aqueous reaction solution, leading to the product in good yields. For the commercial use of the dimethylglucamine, however, this is not advantageous, since dimethylglucamine in solid form is more difficult to handle than a liquid, and it would be advantageous to find synthesis conditions leading directly, without a purification step, to a solution of dimethylglucamine in a water-containing medium. In this case, besides yield and melting point of the recrystallized dimethylglucamine, further quality parameters are relevant, such as, for example, the color of the reaction solution and the amount of starting compounds such as N-methylglucamine, formaldehyde or byproducts such as acids which without recrystallization remain in the product and must therefore be limited.

Other processes describe single-stage processes, but DE-2118283, for example, requires the use of Ag-Pd catalysts and likewise high temperatures of 100° C. to 250° C. The use of an expensive catalyst leads to higher production costs.

It is known, furthermore, that in the preparation of tertiary amines from secondary amines with formaldehyde and hydrogen, the yields achievable are only poor, at below 90%. EP-0142868B1 describes the possibility of achieving better results by using supported catalysts containing a maximum of 10 wt % of Ni, Co, Ru, Rh Pd or Pt on activated carbon. Customary and favorable hydrogenation catalysts such as Raney-Ni or Raney-Co result in poorer product qualities. In this process as well, only gas-chromatographic purities were determined.

In order nevertheless to use these customary catalysts, GB-908203, for example, proposes starting the reaction from 1,3,4,6-tetraacetyl-D-glucosamine and/or using water removers such as zeolites, $MgSO_4$ or $CaCl_2$ (U.S. Pat. No. 4,190,601).

EP-A-663 389 teaches a process for preparing amino alcohols, characterized in that hydroxycarbonyl compounds are reacted with hydrogen and ammonia or with a primary or secondary amine at temperatures of 0 to 300° C. and pressures of 1 to 400 bar in the presence of catalysts whose catalytically active mass consists of 50 to 100 wt % of ruthenium.

The known processes therefore afford only inadequate solutions for the preparation of N,N-dimethylglucamine solutions with low Hazen color numbers from N-methylglucamine. Hence the necessary quality parameters, especially the color of the reaction solution, can often not be maintained (see comparative examples), or the yields are too low. The known processes also lead to higher production costs, since either they require multistage syntheses, purification of the crude reaction solution, or relatively expensive starting substances (e.g., 1,3,4,6-tetraacetyl-D-glucosamine or high-purity N-methylglucamine) or expensive catalysts have to be used. Recycling of the catalysts in order to save costs is likewise not described in the known processes.

There is therefore a need for provision of an inexpensive, catalytic process for preparing N,N-dimethylglucamine solutions from inexpensive, technical or pure N-methylglucamine. For suitability for commercial fields of application such as ink and paint production, crop protection, medicine, and cosmetics, for example, the N,N-dimethylglucamine prepared by the process of the invention, and its aqueous solutions, must meet certain quality requirements in respect of color and maximum amount of defined secondary components, which cannot be achieved with the processes of the prior art.

It has surprisingly been found that in the hydrogenation of the starting materials formaldehyde and N-methylglucamine in the presence of hydrogen, under pressure and with a catalyst, an improved product is obtained when the hydrogenation temperature is lower than that of the prior art.

A subject of the invention is a process for preparing N,N-dimethylglucamine by reacting an aqueous solution of N-methylglucamine first with an aqueous solution of formaldehyde at 15-40° C. and subsequently, at a pressure of 20-120 bar and a temperature T=30-68° C., with hydrogen under metal catalysis, wherein, after absorption of hydrogen has completed at 20-68° C., a further, after-hydrogenation is added at 70-120 bar and at 70-110° C.

Under these reaction conditions it has surprisingly been found that relatively uncolored dimethylglucamine solutions can be obtained.

All percentage figures are percentages by weight, unless any other percentage basis is indicated.

The metal catalyst is preferably an unsupported metal catalyst. In a further embodiment, the metal catalyst comprises cobalt or nickel, preferably Raney nickel.

The hydrogenation takes place preferably at a hydrogen pressure of 20-120 bar, more preferably at 70-110 bar.

The reaction temperature for the hydrogenation in the process of the invention is preferably T=20-68° C., more preferably 35-65° C., especially preferably 40-50° C.

In the process of the invention, the molar ratio of N-methylglucamine: formaldehyde is preferably 1:1 to 1:1.5, more preferably 1:1 to 1:1.2, especially preferably 1:1.01 to 1:1.08.

The process of the invention allows the hydrogenation catalyst to be recycled. The hydrogenation catalyst can preferably be reused more than five times without significant darkening of the color of the end product.

The process of the invention is carried out preferably in a stirred reactor with effective mixing or in a loop reactor with an external pumped circulation and effective mixing. This reactor is temperature-controlled in order to be able to intercept any exothermic or endothermic temperature changes occurring, and to keep the temperature constant throughout the reaction time.

If a dimethylglucamine solution is prepared with the process of the invention, the Hazen color number of a resulting 50% solution of N,N-dimethylglucamine in water is less than 500, preferably <300, more particularly <200.

Based on a 50% dimethylglucamine solution, the solutions prepared by the process of the invention contain less than 2%, preferably less than 1%, more preferably <0.25% of the initial N-methylglucamine product.

Based on a 50% dimethylglucamine solution, the solutions prepared by the process of the invention contain preferably <0.1% of formaldehyde.

Subsequent to the process of the invention, an after-hydrogenation step is added. For this purpose, after the complete addition of the formaldehyde solution and the end of hydrogen absorption, a hydrogenation is performed at 60-110° C. The product obtained from the process of the invention is preferably not isolated before the after-hydrogenation.

Subsequent to the process of the invention, the process of the invention may be followed by a distillation step for removing excess water and the methanol byproduct obtained. In this case, residual amounts of preferably <0.1% of methanol are obtained.

The concentration of the aqueous N-methylglucamine solution used is in the range of 35-70 wt %, preferably 40-65 wt %, especially preferably 50-60 wt %. Technical N-methylglucamine can in principle be prepared from glucose syrup according to WO-92/06073 and without further purification is obtained as an aqueous solution at approximately 60%.

Formaldehyde is used as an aqueous solution, preferably with a concentration between 10 and 60 wt %, especially preferably between 30 and 40 wt %.

The product produced by the process of the invention yields the following quality parameters (based on a 50% solution of N,N-dimethylglucamine in water):

The products have a Hazen color number of less than 500, preferably less than 300; more particularly, of less than 200. This is decisive, for example, for the use in cosmetics or in paints and inks.

The residual N-methylglucamine content (determined by GC) is less than 2 wt %, preferably less than 1 wt %, more particularly less than 0.25 wt %. Elevated values would lead to a higher fraction of secondary amines and to potential nitrosatability, which is disruptive to a large number of applications and formulations.

Furthermore, the presence of short-chain free and also chemically bonded monocarboxylic acids may be a disruption to various applications, as a result, for example, of salt formation. As a lead substance, a description is given here of the formic acid content (determined via ion chromatography (IC)), which with the process of the invention is below 1 wt %, preferably below 0.5 wt %, more particularly below 0.1 wt %.

The content of free and chemically bonded formaldehyde (determined via (PV-LC-114)) with the process described is below 0.5 wt %, preferably below 0.1 wt %, more particularly below 0.05 wt %.

The process of the invention furnishes product which contains low levels of unwanted metallic impurities such as aluminum, cobalt or nickel, for example (determined via ICP-OES). The nickel content is less than 50 ppm, preferably less than 20 ppm, more particularly less than 10 ppm.

Likewise disruptive to the application are volatile organic compounds such as, for example, methanol, the amount of which after appended distillation by the process described is below 0.7 wt %, preferably below 0.5 wt %, especially preferably below 0.1 wt %.

The stated catalysts (e.g., Raney-Ni) remain in the reactor after filtration and are used for further syntheses. This affords a critical advantage over other processes, with which the catalyst cannot be reused or can be reused only a few times, with a considerable increase in the production costs. Any losses of catalyst material due to filtration that do occur can be made up before each new batch.

In order to remove any volatile components present in the reaction solution or to set the desired concentration of water, the reaction solution obtained can be worked up by stripping or distillation or a similar method known to the skilled person. Stripping may take place with addition of nitrogen or water at temperatures between 20-100° C., preferably 30-80° C., especially preferably between 40 and 60° C., under the corresponding vapor pressure of water.

The process of the invention therefore leads to mixtures of N-methylglucamine and water in a proportion, for example, of 1:99 to 99:1, preferably 30:70 to 90:10, especially preferably 45:55 to 80:20.

If even lower concentrations of metals are desired for the use of the product, workup may take place over an ion exchanger or by a similar method known to the skilled person.

Furthermore, the N,N-dimethylglucamine solution prepared by the process of the invention may also be prepared in the form of pure, crystalline N,N-dimethyl-glucamine. This may be done by workup methods known to the skilled person, examples being distillative removal of the water and/or recrystallization from various solvents such as, for instance, alcohol or alcohol/water mixtures, and is important for use in the pharmaceutical and medical sectors.

The process of the invention allows N,N-dimethylglucamine to be produced in an inexpensive and simple process. In comparison to existing processes (e.g., EP-0614881), the process leads to lower color numbers, hence better product quality, and therefore to a broader spectrum of technical usage with reduced costs.

The nickel-containing or cobalt-containing catalyst used leads to a reduction in the costs by comparison with other processes, which require the use of noble metal catalysts such as Ru, Ag—Pd or Pt. The production costs are likewise lowered considerably through the possibility of reusing the catalyst for numerous reaction cycles.

Surprisingly, in contrast to U.S. Pat. No. 4,190,601, it has been found that the presence of water does not disrupt the reaction. Water can therefore be used as solvent. When the described, suitable concentrations are observed, this leads to numerous advantages in connection with handling, such as, for example, a lowering of the viscosity and the prevention of crystallization of the product at room temperature and/or reaction temperature. Using water as a solvent also reduces the costs, lowers the potential for hazard, and avoids toxic/hazardous wastes.

Observing the quality parameters necessary to the application is not adequately described in the case of the known processes described in the prior art, and/or the processes result in relatively poor quality. With the process of the invention it is possible to achieve all necessary quality parameters, particularly the color, using technical N-methylglucamine without prior workup. This in turn leads to a reduction in the costs of production.

EXAMPLES

The dimethylglucamine solutions produced in the examples were characterized by analysis as follows:

Gardner Color Number and Hazen Color Number:

The clear, aqueous dimethylglucamine solutions without any gas bubbles were introduced into 10 mm rectangular cuvettes. The color numbers were measured at room temperature in a LICO 690 colorimeter from Hach Lange.

Total Amine Number by Acid-Base Titration:

The samples, weighed out accurately on an analytical balance, were dissolved in glacial acetic acid and titrated with 0.1 molar perchloric acid in glacial acetic acid, using a titroprocessor from Metrohm.

Solids Content (105° C./2 Hours):

The samples, weighed out precisely, were dried to constant weight in a drying cabinet at 105° C. for two hours by evaporation of the water, and after drying were precisely weighed again.

Water (Karl Fischer titration):

The water content of the precisely weighed-out samples was determined by the Karl Fischer titration method using Karl Fischer solvent and Karl Fischer titrant.

N-methylglucamine, N,N-dimethylglucamine and Sorbitol (GC):

The samples were completely acetylated with a very large excess of acetic anhydride/pyridine at 80° C. The N-methylglucamine, N,N-dimethylglucamine and sorbitol contents were determined by gas chromatography on a 60 m Agilent HP-5 column, using decanol as internal standard and using an FID detector.

Methanol (GC):

The methanol content was determined by a gas-chromatographic method for volatile substances, using isobutanol as internal standard and using a TCD detector.

Formaldehyde (Free and Chemically Bonded):

To release the chemically bonded formaldehyde, the samples were heated with aqueous sulfuric acid in the presence of 2,4-dinitrophenylhydrazine. Through the reaction of the formaldehyde with 2,4-dinitrophenylhydrazine, 2,4-dinitrophenylhydrazone was formed. The 2,4-dinitrophenylhydrazone content was subsequently determined by HPLC liquid chromatography. The free formaldehyde and chemically bonded formaldehyde content was captured as a sum total.

Nitrosamines (Total NNO):

The samples were analyzed for total nitrosamine content in a method based on the ATNC (apparent total nitrosamine content) method. With chemical denitrosation in an acidic medium, nitrogen monoxide was released from the nitrosamines and was subsequently determined quantitatively using a very sensitive detector specific for nitrogen monoxide. Calculation and indication of content were made in the form of the NNO content (>N—N=O with molar mass 44 g/mol).

Nickel (ICP-OES):

The nickel content of the samples was determined by ICP-OES (inductively coupled plasma optical emission spectrometry) in a method based on DIN EN ISO 11885.

Formic Acid (Free and Chemically Bonded, IC):

The samples were pretreated with heating in an aqueous-alkaline medium in order by hydrolysis to liberate the formic acid, bonded chemically in the form of ester and amide. The amount of formic acid or salts thereof already present before the alkaline hydrolysis, and of formic acid and/or salts thereof liberated only by the alkaline hydrolysis, was determined as a sum total by ion chromatography (IC).

Comparative Example 1: Example 2 From EP-0614881

In a 2 liter round-bottom glass flask equipped with stirrer, thermometer and electrical heating under atmospheric pressure, 1500 g of a 43%, aqueous N-methylglucamine solution were produced by diluting a 60% N-methylglucamine solution (Gardner color number 1.7, Hazen color number 263). The 43%, aqueous N-methylglucamine solution was heated to 35° C. with stirring. From a dropping funnel, with further stirring, a total of 288.7 g of a 36.5%, aqueous formaldehyde solution were added dropwise over the course of half an hour at 35° C. The reaction to give the N-methylglucamine-formaldehyde adduct was slightly exothermic. The Gardner color number of the pale-yellow, clear, aqueous N-methylglucamine-formaldehyde adduct solution was 0.8 and the Hazen color number was 151.

Immediately after the end of the dropwise addition, a portion of the aqueous N-methylglucamine-formaldehyde adduct solution amounting to 1300 g was taken from the 2 liter round-bottom glass flask and was introduced at room temperature into a 2 liter stirred autoclave.

The 2 liter stirred autoclave was equipped with stirrer, heating, cooling, supply lines for hydrogen and nitrogen, temperature measurement, pressure measurement, and safety valve. 20.4 g of Raney nickel were introduced under nitrogen into the 2 liter stirred autoclave.

The 2 liter stirred autoclave was closed. Three times, 10 bar of nitrogen were injected, with depressurization each time. Thereafter, three times, 10 bar of hydrogen were injected, with depressurization each time. After the leak test and depressurization, the stirring speed was set to 800 rpm. With further stirring, heating took place to 100° C. and then hydrogen was supplied. The exothermic hydrogenation took place, with renewed injection of the hydrogen consumed, at 800 rpm, 100° C. and a hydrogen pressure of 30 bar. After the end of the evident absorption of hydrogen, stirring was continued for two hours at 100° C. and a hydrogen pressure of 30 bar. This was followed by cooling to 30° C., depressurization, purging with nitrogen, and the emptying of the 2 liter stirred autoclave. The Raney nickel catalyst was separated off by a pressure filtration under nitrogen. The liquid filtrate was dark brown and had a Gardner color number of 8.

This dark brown filtrate was subjected to initial distillation in a rotary evaporator at 60° C. under a pressure of 20 mbar. The distillate contained primarily water, a little methanol, and traces of other low boilers. The viscous N,N-dimethylglucamine having undergone initial distillation was adjusted to an active ingredient content of 51% and DI water content of 49% by addition of DI water with thorough mixing at 60° C. This product solution was subjected to analysis. Apart from the losses involved in emptying the autoclave and working up the solution, the yield of dissolved N,N-dimethylglucamine in the DMG 50 was virtually quantitative.

The product obtained was characterized as follows:
Appearance at 20° C.: clear, liquid, dark brown
Gardner color number: 9.4
Hazen color number: not measurable, since too dark
Total amine number (titration): 133 mg KOH/g
Solids content (105° C./2 hours): 51.4% (m/m)
Water (Karl-Fischer titration): 49% (m/m)
N-Methylglucamine (GC): 0.91% (m/m)
N,N-Dimethylglucamine (GC): 44.5% (m/m)
Sorbitol (GC): 0.6% (m/m)
Methanol (GC): <0.1% (m/m)
Formaldehyde (free and chemically bonded, LC): 0.026% (m/m)
Nitrosamines (total NNO): <50 µg/kg
Nickel (ICP-OES): 35 µg/g
Formic acid (free and chemically bonded) 0.70% (m/m)

Comparative Example 2: As Per Example 3 From EP-0614881

In a 2 liter round-bottom glass flask equipped with stirrer, thermometer and electrical heating under atmospheric pressure, 1500 g of a 43%, aqueous N-methylglucamine solution were produced by diluting a 60%, technical N-methylglucamine solution (Gardner color number 1.7, Hazen color number 263) with DI water.

The 43%, aqueous N-methylglucamine solution was heated to 35° C. with stirring. From a dropping funnel, with further stirring, a total of 288.7 g of a 36.5%, aqueous formaldehyde solution were added dropwise over the course of half an hour at 35° C. The reaction to give the N-methylglucamine-formaldehyde adduct was slightly exothermic. Thereafter the clear, pale yellow reaction mixture was additionally stirred further for an hour at 35° C. The Gardner color number of this pale-yellow, aqueous N-methylglucamine-formaldehyde adduct solution was 0.8 and the Hazen color number was 162.

Thereafter, a portion of the aqueous N-methylglucamine-formaldehyde adduct solution amounting to 1300 g was taken from the 2 liter round-bottom glass flask and was introduced at room temperature into a 2 liter stirred autoclave.

The 2 liter stirred autoclave was equipped with stirrer, heating, cooling, supply lines for hydrogen and nitrogen, temperature measurement, pressure measurement, and safety valve. 20.4 g of Raney nickel were introduced under nitrogen into the 2 liter stirred autoclave.

The 2 liter stirred autoclave was closed. Three times, 10 bar of nitrogen were injected, with depressurization each time. Thereafter, three times, 10 bar of hydrogen were injected, with depressurization each time. After the leak test and depressurization, the stirring speed was set to 800 rpm. With further stirring, heating took place to 125° C. and then hydrogen was supplied. The exothermic hydrogenation took place, with renewed injection of the hydrogen consumed, at 800 rpm, 130° C. and a hydrogen pressure of 100 bar. After the end of the evident absorption of hydrogen, stirring was continued for two hours at 130° C. and a hydrogen pressure of 100 bar. This was followed by cooling to 30° C., depressurization, purging with nitrogen, and the emptying of the 2 liter stirred autoclave. The Raney nickel catalyst was separated off by a pressure filtration under nitrogen. The liquid filtrate was deeply dark brown and had a Gardner color number of 13.4.

This deeply dark brown filtrate was subjected to initial distillation in a rotary evaporator at 60° C. under a pressure of 20 mbar. The distillate contained primarily water, a little methanol, and traces of other low boilers. The viscous N,N-dimethylglucamine having undergone initial distillation was adjusted to an active ingredient content of 51% and DI water content of 49% by addition of DI water with thorough mixing at 60° C. The resulting product solution was subjected to analysis. Apart from the losses involved in emptying the autoclave and working up the solution, the yield of dissolved N,N-dimethylglucamine in the DMG 50 was virtually quantitative.

The product obtained was characterized as follows:
Appearance at 20° C.: clear, liquid, deeply dark brown
Gardner color number: 16.9
Hazen color number: not measurable, since too dark
Total amine number (titration): 133 mg KOH/g
Solids content (105° C./2 hours): 52.6% (m/m)
Water (Karl-Fischer titration): 49% (m/m)
N-Methylglucamine (GC): 6.0% (m/m)
N,N-Dimethylglucamine (GC): 35.9% (m/m)
Sorbitol (GC): 0.6% (m/m)
Methanol (GC): <0.1% (m/m)
Formaldehyde (free and chemically bonded, LC): 0.012% (m/m)
Nitrosamines (total NNO): <50 µg/kg
Nickel (ICP-OES): 29 µg/g
Formic acid (free and chemically bonded) 0.90% (m/m)

| Example | 1-stage/ 2-stage | Hydrogenation pressure | Hydrogenation temperature [° C.] | Color (GCN/ Hazen) | NMG [%] | Ni [ppm] | Formaldehyde [%] |
|---|---|---|---|---|---|---|---|
| 1 (comp.) | 2-stage | 30 | 100 | 9.4/— | 0.91 | 35 | 0.03 |
| 2 (comp.) | 2-stage | 100 | 130 | 16.9/— | 6.0 | 29 | 0.01 |
| 1 | 2-stage | 30 | 20-60, then 100 | 1.5/246 | 0.16 | 5 | 0.02 |
| 2 | 2-stage | 100 | 20-60, then 130 | 3.5/485 | 0.29 | 2 | 0.01 |
| 3 | 2-stage | 100 | 20-40, then 90 | 1.0/158 | 0.12 | 4 | 0.03 |

Example 1

In a 2 liter round-bottom glass flask equipped with stirrer, thermometer and electrical heating under atmospheric pressure, 1500 g of a 43%, aqueous N-methylglucamine solution were produced by diluting a 60%, technical N-methyl-glucamine solution (Gardner color number 1.7, Hazen color number 263) with DI water.

The 43%, aqueous N-methylglucamine solution was heated to 35° C. with stirring. From a dropping funnel, with further stirring, a total of 288.7 g of a 36.5%, aqueous formaldehyde solution were added dropwise over the course of half an hour at 35° C. The reaction to give the N-methylglucamine-formaldehyde adduct was slightly exothermic. The Gardner color number of the pale-yellow, clear, aqueous N-methylglucamine-formaldehyde adduct solution was 0.8 and the Hazen color number was 154.

Immediately after the end of the dropwise addition, a portion of the aqueous N-methylglucamine-formaldehyde adduct solution amounting to 1300 g was taken from the 2 liter round-bottom glass flask and was introduced at room temperature into a 2 liter stirred autoclave.

The 2 liter stirred autoclave was equipped with stirrer, heating, cooling, supply lines for hydrogen and nitrogen, temperature measurement, pressure measurement, and safety valve. 20.4 g of Raney nickel were introduced under nitrogen into the 2 liter stirred autoclave.

The 2 liter stirred autoclave was closed. Three times, 10 bar of nitrogen were injected, with depressurization each time. Thereafter, three times, 10 bar of hydrogen were injected, with depressurization each time. After the leak test and depressurization, the stirring speed was set to 800 rpm. At 20° C., hydrogen was injected. The exothermic hydrogenation commenced directly with supply of the consumed hydrogen at 15-25 bar hydrogen pressure and heating to 60° C., and then the recognizable hydrogen absorption was at an end. This was followed by further heating to 100° C. and then by further stirring for two hours at 800 rpm, 100° C. and 30 bar hydrogen pressure. There was cooling to 30° C., depressurization, purging with nitrogen, and the emptying of the 2 liter stirred autoclave. The Raney nickel catalyst was separated off by a pressure filtration under nitrogen. The liquid filtrate was pale yellow and had a Gardner color number of 0.7 and a Hazen color number of 130.

This pale-yellow filtrate was subjected to initial distillation in a rotary evaporator at 60° C. under a pressure of 20 mbar. The distillate contained primarily water, a little methanol, and traces of other low boilers. The viscous N,N-dimethylglucamine having undergone initial distillation was adjusted to an active ingredient content of 51% and DI water content of 49% by addition of DI water with thorough mixing at 60° C. This mixture was subjected to analysis. Apart from the losses involved in emptying the autoclave and working up the solution, the yield of dissolved N,N-dimethylglucamine in the product was virtually quantitative.

The product obtained was characterized as follows:
Appearance at 20° C. clear, liquid, pale yellow
Gardner color number: 1.5
Hazen color number: 246
Total amine number (titration): 132 mg KOH/g
Solids content (105° C./2 hours): 50.7% (m/m)
Water (Karl-Fischer titration): 49% (m/m)
N-Methylglucamine (GC): 0.16% (m/m)
N,N-Dimethylglucamine (GC): 45.1% (m/m), depending on the NMG grade
Sorbitol (GC): 0.7% (m/m)
Methanol (GC): <0.1% (m/m)
Formaldehyde (free and chemically bonded, LC): 0.022% (m/m)
Nitrosamines (total NNO): <50 µg/kg
Nickel (ICP-OES): 5 µg/g
Formic acid (free and chemically bonded) 0.25% (m/m) (ion chromatography after alkaline hydrolysis, IC)

Example 2

In a 2 liter round-bottom glass flask equipped with stirrer, thermometer and electrical heating under atmospheric pressure, 1500 g of a 43%, aqueous N-methylglucamine solution were produced by diluting a 60%, technical N-methylglucamine solution (Gardner color number 1.7, Hazen color number 263) with DI water.

The 43%, aqueous N-methylglucamine solution was heated to 35° C. with stirring. From a dropping funnel, with further stirring, a total of 288.7 g of a 36.5%, aqueous formaldehyde solution were added dropwise over the course of half an hour at 35° C. The reaction to give the N-methylglucamine-formaldehyde adduct was slightly exothermic. Thereafter, the clear, pale-yellow reaction mixture was additionally stirred for another hour at 35° C. The Gardner color number of this pale-yellow, aqueous N-methylglucamine-formaldehyde adduct solution was 0.8 and the Hazen color number was 162.

Immediately after the end of the dropwise addition, a portion of the aqueous N-methylglucamine-formaldehyde adduct solution amounting to 1300 g was taken from the 2 liter round-bottom glass flask and was introduced at room temperature into a 2 liter stirred autoclave.

The 2 liter stirred autoclave was equipped with stirrer, heating, cooling, supply lines for hydrogen and nitrogen, temperature measurement, pressure measurement, and safety valve. 20.4 g of Raney nickel were introduced under nitrogen into the 2 liter stirred autoclave.

The 2 liter stirred autoclave was closed. Three times, 10 bar of nitrogen were injected, with depressurization each time. Thereafter, three times, 10 bar of hydrogen were injected, with depressurization each time. After the leak test and depressurization, the stirring speed was set to 800 rpm. At 20° C., hydrogen was injected. The exothermic hydrogenation commenced directly with supply of the consumed hydrogen at 15-25 bar hydrogen pressure and heating to 60° C., and then the recognizable hydrogen absorption was at an end. This was followed by further heating to 130° C. and then by further stirring for two hours at 800 rpm, 130° C. and 100 bar hydrogen pressure. There was cooling to 30° C., depressurization, purging with nitrogen, and the emptying of the 2 liter stirred autoclave. The Raney nickel catalyst was separated off by a pressure filtration under nitrogen. The liquid filtrate was pale yellow and had a Gardner color number of 0.3 and a Hazen color number of 56.

This pale-yellow filtrate was subjected to initial distillation in a rotary evaporator at 60° C. under a pressure of 20 mbar. The distillate contained primarily water, a little methanol, and traces of other low boilers. The viscous N,N-dimethylglucamine having undergone initial distillation was adjusted to an active ingredient content of 50% and DI water content of 50% by addition of DI water with thorough mixing at 60° C. This mixture was subjected to analysis. Apart from the losses involved in emptying the autoclave and working up the solution, the yield of dissolved N,N-dimethylglucamine in the DMG 50 was virtually quantitative.

The product obtained was characterized as follows:
Appearance at 20° C.: clear, liquid, deeply yellow
Gardner color number: 3.5
Hazen color number: 485
Total amine number (titration): 129 mg KOH/g
Solids content (105° C./2 hours): 49.7% (m/m)
Water (Karl-Fischer titration): 50% (m/m)
N-Methylglucamine (GC): 0.29% (m/m)
N,N-Dimethylglucamine (GC): 43.5% (m/m)
Sorbitol (GC): 0.6% (m/m)
Methanol (GC): <0.1% (m/m)
Formaldehyde (free and chemically bonded, LC): 0.0097% (m/m)
Nitrosamines (total NNO): <50 µg/kg
Nickel (ICP-OES): 2 µg/g
Formic acid (free and chemically bonded) 0.18% (m/m) (ion chromatography after alkaline hydrolysis, IC)

Example 3

In a 2 liter round-bottom glass flask equipped with stirrer, thermometer and electrical heating under atmospheric pressure, 1500 g of a 43%, aqueous
N-methylglucamine solution were produced by diluting a 60%, technical N-methyl-glucamine solution (Gardner color number 1.7, Hazen color number 263) with DI water.

The 43%, aqueous N-methylglucamine solution was heated to 35° C. with stirring.

From a dropping funnel, with further stirring, a total of 288.7 g of a 36.5%, aqueous formaldehyde solution were added dropwise over the course of half an hour at 35° C. The reaction to give the N-methylglucamine-formaldehyde adduct was slightly exothermic. The Gardner color number of the pale-yellow, clear, aqueous N-methylglucamine-formaldehyde adduct solution was 0.8 and the Hazen color number was 154.

Immediately after the end of the dropwise addition, a portion of the aqueous N-methylglucamine-formaldehyde adduct solution amounting to 1300 g was taken from the 2 liter round-bottom glass flask and was introduced at room temperature into a 2 liter stirred autoclave.

The 2 liter stirred autoclave was equipped with stirrer, heating, cooling, supply lines for hydrogen and nitrogen, temperature measurement, pressure measurement, and safety valve. 20.4 g of Raney nickel were introduced under nitrogen into the 2 liter stirred autoclave.

The 2 liter stirred autoclave was closed. Three times, 10 bar of nitrogen were injected, with depressurization each time. Thereafter, three times, 10 bar of hydrogen were injected, with depressurization each time. After the leak test and depressurization, the stirring speed was set to 800 rpm. At 20° C., hydrogen was injected. The exothermic hydrogenation commenced directly with supply of the consumed hydrogen at 15-25 bar hydrogen pressure. By cooling, the autoclave was maintained within a temperature range of 30-40° C. until the recognizable hydrogen absorption was at an end. This was followed by further heating to 90° C. and then by further stirring for two hours at 800 rpm, 90° C. and 30 bar hydrogen pressure. There was cooling to 30° C., depressurization, purging with nitrogen, and the emptying of the 2 liter stirred autoclave. The Raney nickel catalyst was separated off by a pressure filtration under nitrogen. The liquid filtrate was pale yellow and had a Gardner color number of 0.6 and a Hazen color number of 110.

This pale-yellow filtrate was subjected to initial distillation in a rotary evaporator at 60° C. under a pressure of 20 mbar. The distillate contained primarily water, a little methanol, and traces of other low boilers. The viscous N,N-dimethylglucamine having undergone initial distillation was adjusted to an active ingredient content of 51% and DI water content of 49% by addition of DI water with thorough mixing at 60° C. This mixture was subjected to analysis. Apart from the losses involved in emptying the autoclave and working up the solution, the yield of dissolved N,N-dimethylglucamine in the product was virtually quantitative.

The product obtained was characterized as follows:
Appearance at 20° C.: clear, liquid, pale yellow
Gardner color number: 1.0
Hazen color number: 158
Total amine number (titration): 131 mg KOH/g
Solids content (105° C./2 hours): 50.8% (m/m)
Water (Karl-Fischer titration): 49.1% (m/m)
N-Methylglucamine (GC): 0.12% (m/m)
N,N-Dimethylglucamine (GC): 44.6% (m/m)
Sorbitol (GC): 0.6% (m/m)
Methanol (GC): <0.1% (m/m)
Formaldehyde (free and chemically bonded, LC): 0.025% (m/m)
Nitrosamines (total NNO): <50 µg/kg
Nickel (ICP-OES): 4 µg/g
Formic acid (free and chemically bonded) 0.21% (m/m) (ion chromatography after alkaline hydrolysis, IC)

The invention claimed is:

1. A process for preparing N,N-dimethylglucamine comprising the step of reacting an aqueous solution of N-methylglucamine first with an aqueous solution of formaldehyde at 15-40° C. and subsequently, at a pressure of 20-120 bar and a temperature T=30-68° C., with hydrogen under metal catalysis, wherein, after absorption of hydrogen has completed at 20-68° C., a further, after-hydrogenation is added at 70-120 bar and at 70-110° C.

2. The process as claimed in claim 1, wherein the metal catalyst is Raney nickel.

3. The process as claimed in claim 1, which is carried out at a hydrogen pressure of 70-110 bar.

4. The process as claimed in claim 1, wherein the hydrogenation is carried out at 35-65° C.

5. The process as claimed in claim 1, wherein the molar ratio of N-methylglucamine to formaldehyde is 1:1 to 1:1.5.

6. The process as claimed in claim 1, wherein the hydrogenation catalyst is reused more than 5 times.

7. The process as claimed in claim 1, wherein reaction takes place in a stirred reactor or loop reactor.

8. The process as claimed in claim 1, wherein the remaining N-methylglucamine content is <2wt %.

9. The process as claimed in claim 1, wherein the residual formaldehyde content is <0.1 wt %.

10. The process as claimed in claim 1, in which the Hazen color number of the resulting solution of N,N-dimethylglucamine is <500.

11. The process as claimed in claim 1, in which the molar ratio of N-methylglucamine to formaldehyde is 1:1 to 1:1.2.

12. The process as claimed in claim 1, in which the molar ratio of N-methylglucamine to formaldehyde is 1:1.01 to 1:1.08.

13. The process as claimed in claim 1, wherein the residual N-methylglucamine content is <1 wt %.

14. The process as claimed in claim 1, wherein the residual N-methylglucamine content is <0.25 wt %.

15. The process as claimed in claim 1, wherein the hydrogenation is carried out at 40-50° C.

* * * * *